(12) United States Patent
Zadgaonkar et al.

(10) Patent No.: US 10,593,351 B2
(45) Date of Patent: Mar. 17, 2020

(54) SYSTEM AND METHOD FOR ESTIMATING HORMONE LEVEL AND PHYSIOLOGICAL CONDITIONS BY ANALYSING SPEECH SAMPLES

(71) Applicants: Ajit Arun Zadgaonkar, Riverside, CA (US); Arun Shrihari Zadgaonkar, Riverside, CA (US)

(72) Inventors: Ajit Arun Zadgaonkar, Riverside, CA (US); Arun Shrihari Zadgaonkar, Riverside, CA (US)

(*) Notice: Subject to any disclaimer, the term of this patent is extended or adjusted under 35 U.S.C. 154(b) by 57 days.

(21) Appl. No.: 15/968,734

(22) Filed: May 1, 2018

(65) Prior Publication Data

US 2018/0322893 A1   Nov. 8, 2018

(30) Foreign Application Priority Data

May 3, 2017   (IN) .............................. 201721015661

(51) Int. Cl.

| | |
|---|---|
| *G10L 25/66* | (2013.01) |
| *A61B 5/00* | (2006.01) |
| *G10L 15/02* | (2006.01) |
| *A61B 5/145* | (2006.01) |
| *G10L 15/08* | (2006.01) |
| *G10L 17/26* | (2013.01) |
| *G10L 15/26* | (2006.01) |
| *G10L 25/15* | (2013.01) |

(52) U.S. Cl.
CPC .......... *G10L 25/66* (2013.01); *A61B 5/14546* (2013.01); *A61B 5/4803* (2013.01); *G10L 15/02* (2013.01); *G10L 15/08* (2013.01); *G10L 15/265* (2013.01); *G10L 17/26* (2013.01); *A61B 5/4227* (2013.01); *G10L 25/15* (2013.01); *G10L 2015/025* (2013.01)

(58) Field of Classification Search
CPC ....... G10L 15/08; G10L 15/265; G10L 17/26; A61B 5/4803
See application file for complete search history.

(56) References Cited

U.S. PATENT DOCUMENTS

| | | | | |
|---|---|---|---|---|
| 5,870,709 A | * | 2/1999 | Bernstein ................. | G09B 7/04 434/156 |
| 6,904,408 B1 | * | 6/2005 | McCarthy ............ | A61B 5/6815 705/2 |
| 9,741,258 B1 | * | 8/2017 | Chetlur .................... | G09B 5/12 |

(Continued)

*Primary Examiner* — Eric Yen

(57) ABSTRACT

The present disclosure describes a system and method for estimating hormone levels and physiological conditions of a user by analysing speech samples of said user. A user device of the user may record specifics of speech and use these specifics of speech as a speech sample of user's utterance. The user device may transmit the speech samples to a backend system. The system may isolate phonation segments from the speech samples. The system may filter the one or more phonation segments. The system may isolate uttered speech segments from the one or more phonation segments. The system may perform an acoustic-phonetic analysis of the uttered speech segments. The acoustic-phonetic analysis may use plurality of features for the analysis. The IPA phonemes may be used to derive speech markers that correspond to specific hormones and levels thereof. The system may generate a hormone level report which is transmitted to the user.

12 Claims, 3 Drawing Sheets

(56) References Cited

U.S. PATENT DOCUMENTS

| | | | | |
|---|---|---|---|---|
| 2002/0143531 | A1* | 10/2002 | Kahn | G10L 15/26 704/235 |
| 2005/0228673 | A1* | 10/2005 | Nefian | G10L 15/25 704/270 |
| 2006/0053012 | A1* | 3/2006 | Eayrs | G10L 21/06 704/251 |
| 2007/0213981 | A1* | 9/2007 | Meyerhoff | G10L 17/26 704/243 |
| 2008/0208538 | A1* | 8/2008 | Visser | G10L 21/0272 702/190 |
| 2008/0255842 | A1* | 10/2008 | Simhi | G10L 25/78 704/246 |
| 2013/0051271 | A1* | 2/2013 | Cao | H04L 41/5067 370/252 |
| 2014/0112556 | A1* | 4/2014 | Kalinli-Akbacak | G10L 25/63 382/128 |
| 2015/0064669 | A1* | 3/2015 | Golan | G09B 19/00 434/236 |
| 2017/0000397 | A1* | 1/2017 | Mitsuyoshi | A61B 5/741 |
| 2018/0190284 | A1* | 7/2018 | Singh | G10L 25/66 |

\* cited by examiner

SYSTEM AND METHOD FOR ESTIMATING HORMONE LEVEL AND PHYSIOLOGICAL CONDITIONS BY ANALYSING SPEECH SAMPLES

CROSS-REFERENCE TO RELATED APPLICATIONS AND PRIORITY

The present application claims priority from Indian provisional patent application no. 201721015661 filed on the 3$^{rd}$ day of May 2017, the details of which are incorporated herein by a reference.

TECHNICAL FIELD

The present disclosure described herein, in general, relates to a system and method for analysis of speech samples of a user and thereby determination or prediction of hormone levels and the physiological conditions of the user.

BACKGROUND

There are several critical hormones which regulate the functioning of the various gynaecological phases (regular menses, the fertility period, and the peri- or 10 post-menopausal stage) women go through during their life. These hormones play a critical role in pregnancy as well. Having healthy and normal levels of these hormones plays a key role in the well-being of women of all ages. This is true for men as well, as there are hormones which play a critical role in men's health, too. An imbalance in these hormone levels can be associated with many health issues such as infertility, pregnancy problems, fatigue, sleep disorders, viral infections like EBV and herpes, allergies, anxiety disorders, migraines, digestive disorders, depression, premenstrual syndrome (PMS), cancer, cardiovascular disease, weight gain, autoimmune diseases, insomnia, and diabetes. It has been well-established that hormonal imbalance gets more severe gradually with age and is harder to diagnose initially.

Therefore, hormone level tests and physiological condition tests are very important. The tests should be accurately done and should be non-invasive. Hormone level tests are currently conducted by pathological laboratory analysis of saliva and blood samples. Both methods are invasive in nature, often require tests be administered by medically-trained professionals and usually require patients to travel to clinics or hospitals or laboratory offices. These invasive tests are not comfortable for many, usually expensive, and impose a logistical burden on patients who might not be able to travel, and often require fasting prior to the tests.

Thus, in view of the above, one can conclude that there is a long-felt need for a method and system for estimating the hormone level and predicting physiological conditions, so that the user/patient can easily check their hormone levels. The method should be easy, accurate and non-invasive, and should enable timely evaluation of hormone levels and related health conditions at any time, without imposing any burden of conducting a laboratory or hospital test. The method should not require a medically-trained professional for performing tests.

SUMMARY

This summary is provided to introduce the concepts related to a system and method for estimating hormone level and physiological conditions by analyzing speech samples of a user and the concepts are further described in the detailed description. This summary is not intended to identify essential features of the claimed disclosure nor it is intended to use in determining or limiting the scope of claimed subject matter.

In one embodiment, a system for estimating hormone level and physiological conditions of a user is disclosed. The system may comprise a processor and a memory coupled with the processor. The processor may be configured to execute a plurality of programmed instructions stored in the memory. The processor may execute a programmed instruction for guiding a user to utter specifics of a speech via a user device communicatively coupled with the processor. Further, the processor may execute a programmed instruction for recording one or more speech samples associated with the user based upon the specifics of speech uttered by the user. The processor may further execute a programmed instruction for isolating one or more phonation segments from the one or more speech samples. Further, the processor may execute a programmed instruction for filtering one or more phonation segments to remove noise from the one or more phonation segments. The processor may further execute a programmed instruction for isolating one or more uttered speech segments from the one or more phonation segments filtered. Further, the processor may execute a programmed instruction for performing acoustic-phonetic analysis of the one or more uttered speech segments to extract one or more speech features. Furthermore, the processor may execute a programmed instruction for determining one or more speech markers and the corresponding hormone level of the user based upon the one or more speech features.

In accordance with aspects of the present disclosure, the specifics of speech may comprise attributes selected from a group comprising of a frequency and formants. Further, the specifics of speech may include, but not limited to, one or more of words, letters, phonations, and the like.

In accordance with aspects of the present disclosure, the one or more speech features may include, but not limited to, utterance of the user, vowel and consonants under isolated and/or vowel consonant (VC), consonant Vowel (CV) environment, formants of the utterance, pitch of the utterance, vocal intensity of the utterance, speech quality of the utterance, vowel onset point (VOP), energy transition, values of dispersion and bandwidth, voice onset time (VOT), articulatory rate, shimmer, jitter, spectrogram, and the like.

In accordance with aspects of the present disclosure, the speech markers corresponding to the hormone levels may include, but not limited to, HCG speech marker, estrogen speech marker, progesterone speech marker, LH speech marker, and FSH speech marker. Further, the speech markers and the corresponding hormone levels may be determined using International Phonetic alphabets (IPA) phonemes selected from a group comprising semi-vowel, bilabial nasal consonant and voiced bilabial consonant.

In accordance with an aspect of the present disclosure, a hormone level corresponding to the Follicle Stimulating Hormone (FSH) may be an index of a speech marker consisting of a ratio of the pitch and formants of the semi-vowels, bilabial nasal consonant and voiced bilabial consonants.

In accordance with an aspect of the present disclosure, a hormone level corresponding to the Luteinizing hormone (LH) may be an index of a speech marker consisting of a ratio of formants of the semi-vowels, bilabial nasal consonant and voiced bilabial consonants.

In accordance with an aspect of the present disclosure, a hormone level corresponding to the estrogen hormone may be an index of a speech marker consisting of half of the difference of the formant values multiplied by frequency perturbation factor of the semi-vowels, bilabial nasal consonants and voiced bilabial consonants.

In accordance with an aspect of the present disclosure, a hormone level corresponding to the progesterone hormone may be determined from the speech markers of the semi-vowels, from the ratio of formants.

In accordance with an aspect of the present disclosure, a hormone level corresponding to the Human chorionic gonadotropin (hCG) hormone is an index of a speech marker consisting of sum of pitch and formant values of the semi-vowels, bilabial nasal consonant and voiced bilabial consonants.

In accordance with an aspect of the present disclosure, the processor may further execute a programmed instruction for generating reports based upon the estimation of hormonal levels of the user. The reports generated may include separate reports for one or more of estrogen, progesterone, Luteinizing Hormone (LH), Follicle Stimulating Hormone (FSH) and other human body hormones.

In another embodiment, a method for estimating hormone level and physiological conditions of a user is disclosed. The method may include interactively guiding, via a user device communicatively coupled with a processor, a user to utter specifics of a speech via a user. Further, the method may include recording, via the user device, one or more speech samples associated with the user based upon the specifics of speech uttered by the user. The method may further include isolating, via the processor, one or more phonation segments from the one or more speech samples. Further, the method may include filtering, via the processor, one or more phonation segments to remove noise from the one or more phonation segments. The method may further include isolating, via the processor, one or more uttered speech segments from the one or more phonation segments filtered. Further, the method may include performing, via the processor, acoustic-phonetic analysis of the one or more uttered speech segments to extract one or more speech features. Furthermore, the method may include determining, via the processor, one or more speech markers and the corresponding hormone level of the user based upon the one or more speech features.

In accordance with an aspect of the present disclosure, the method may further include generating, via the processor, reports based upon the estimation of hormonal levels of the user. The reports generated may include separate reports for one or more of estrogen, progesterone, Luteinizing Hormone (LH), Follicle Stimulating Hormone (FSH) and other human body hormones.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

Figure 1:
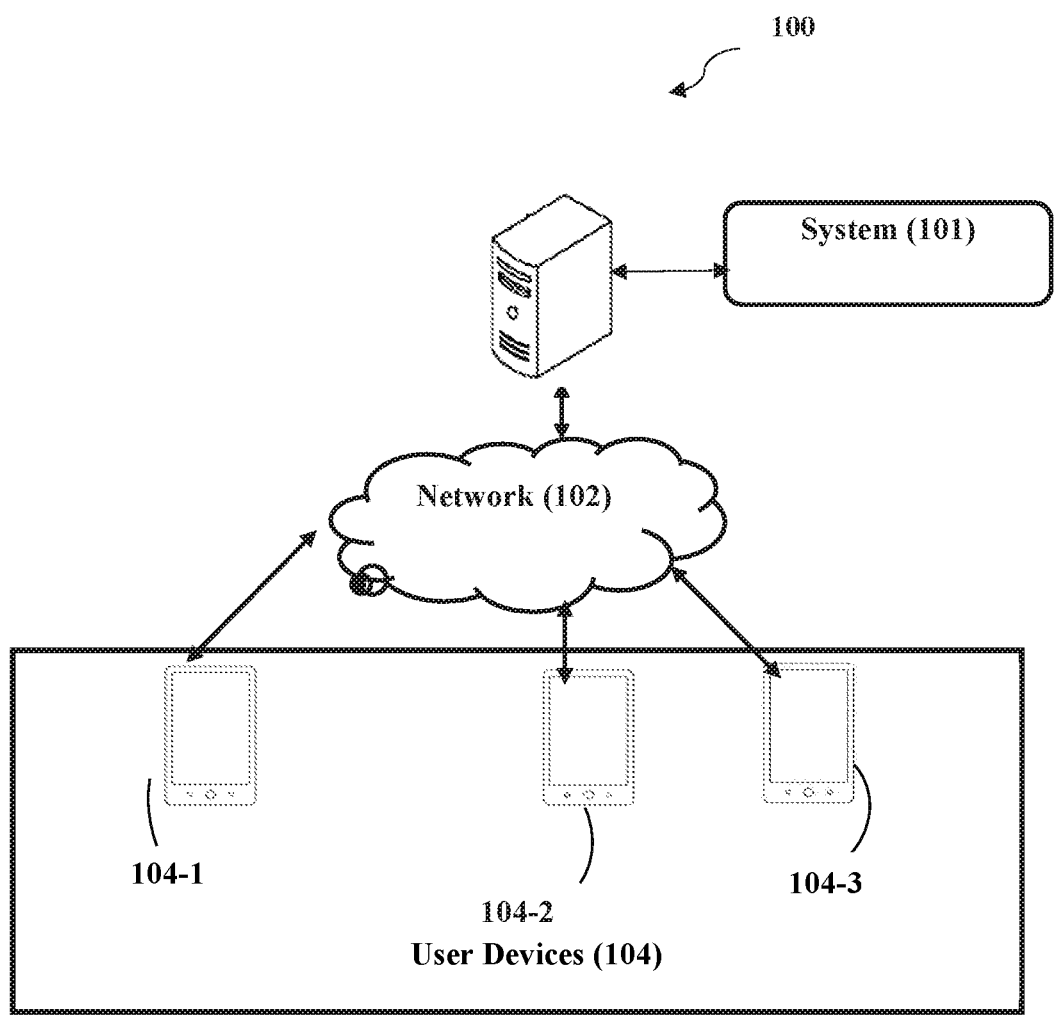
FIG. 1 illustrates a network implementation (100) of a system (101) for determining hormone level and physiological conditions of a user by analysing speech samples of the said user, in accordance with an embodiment of a present disclosure.

FIG. 1 illustrates a network implementation (100) of a system (101) for estimating hormone level and physiological conditions of a user by analysing speech samples of the said user, in accordance with an embodiment of a present disclosure. In an embodiment, though the present disclosure is explained considering that the system 101 is implemented as a server, it may be understood that the system 101 may also be implemented in a variety of user devices, such as a but are not limited to, a portable computer, a personal digital assistant, a handheld device, a mobile, a laptop computer, a desktop computer, a notebook, a workstation, a mainframe computer, and the like. In some embodiments, the system 101 may be implemented in a cloud-based computing environment, a distributing computing environment, and the like.

In an embodiment, the system 101 may be connected to a user device 104 over a network 102. It may be understood that the system 101 may be accessed by multiple users through one or more user devices 104-1, 104-2, 104-3 . . . 104-n, collectively referred to as user device 104 hereinafter, or applications residing on the user device 104. In an embodiment, as illustrated in FIG. 1, the system 101 may accept information provided by multiple users 104-1,104-2,104-3 using the user device 104 to register the respective user with the system 101. The user devices 104 may accessed the system 101 via the network 102. In an embodiment, the network 102 may be a wireless network, a wired network or a combination thereof. The network 102 may be accessed by the device using wired or wireless network connectivity means including any updated communications technology.

Figure 2:
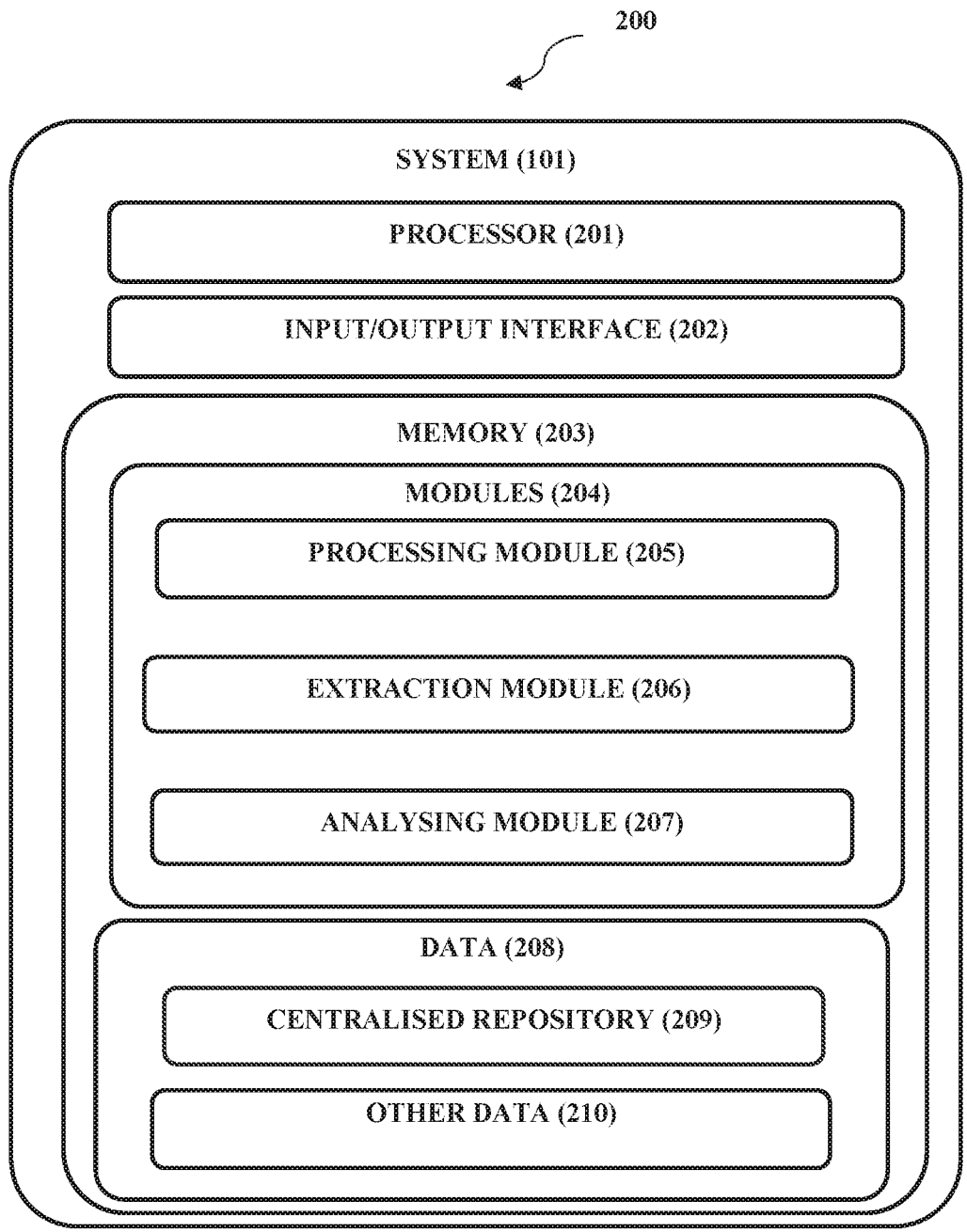
FIG. 2 illustrates the system (101) along with components of the system 101, in accordance with an embodiment of a present disclosure.

Now referring to FIG. 2 illustrates the system 101 and the components of the system 101 in accordance with an embodiment of the present disclosure. As shown, the system may include at least one processor 201, an input/output (I/O) interface 202, a memory 203, modules 204 and data 208. In one embodiment, the at least one processor 201 is configured to fetch and execute computer-readable instructions stored in the memory 203.

In one embodiment, the I/O interface 202 may include a variety of software and hardware interfaces, for example, a web interface, a graphical user interface, and the like. The I/O interface 202 may allow the system to interact with the user device 104. Further, the I/O interface 202 may enable the system to communicate with other computing devices. The I/O interface 202 can facilitate multiple communications within a wide variety of networks and protocol types, including wired networks, for example, LAN, cable, etc., and wireless networks, such as WLAN, cellular, or satellite.

In one embodiment, the I/O interface 202 is an interaction platform that facilitates interaction between the user device 104 and the system. The I/O interface 202 may allow commands for a command line interface or a geographical interface (GUI) which may enable a user to create, modify and delete either of data, metadata, program, logic, algorithm, parameters associated with encryption method, encryption program and encryption language.

In one embodiment, the memory 203 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and memory cards. The memory 203 may include modules 204 and data 208.

In one embodiment, the modules 204 may include routines, programs, objects, components, data structure, etc., which performs particular tasks, functions or implement abstract data types. The modules 204 may further include a processing module 205, an extraction module 206, and an analysing module 207. The data 208 may include a centralized repository 209 and other data 210.

In one embodiment, the user device 104 may interactively guide a user to utter specifics of speech. The user device 104 may record these specifics of speech using a built-in sound recorder and may use these specifics of speech as a speech sample of user's utterance. The speech samples may be stored in a local storage of the user device 104. The user device 104 may further record one or more metadata of the user. The user device may transmit the speech samples and the metadata to the system 101 for further processing and analysis.

In one embodiment, the speech samples and the metadata may be stored within the centralized repository 209. In one embodiment, the specifics of speech may include, but not limited to, specific words, letters, phonation, and the like. The metadata of the user may include, but are not limited to, user's name, age, location, and the like.

In one embodiment, the processing module 205 may process the speech samples by isolating the one or more phonation segments from the speech samples. The processing module 205, may isolate phonation samples for isolating phonation sound using existing phonation isolation techniques/algorithms known in the art. The processing module 205, may further filter the one or more phonation segments in order to remove noise from the one or more phonation segments using existing phonation segment filtration techniques/algorithms known in the art. The processing module 205 may further isolate the uttered speech segments from the one or more phonation segments.

In one embodiment, the extraction module 206, via a processor, may extract the speech features from the uttered speech segments using existing speech feature extraction techniques/algorithms known in the art. The speech features may include, but are not limited to, utterance of the user, vowel and consonants under isolated and/or vowel consonant (VC), consonant vowel (CV) environment, formants of the utterance, pitch of the utterance, vocal intensity of the utterance, speech quality of the utterance, Vowel Onset Point (VOP), energy transition, values of dispersion and bandwidth, Voice Onset Time (VOT), articulatory rate, shimmer, jitter, spectrogram, etc. The speech features may form a unique set of properties that belong to the user. The unique set of properties that corresponds to the user's current hormone level and physiological condition may be referred herein as speech markers.

In one embodiment, the speech markers associated with specific hormones may be used to determine the exact level of a particular hormone in the user. The hormones may be Follicle Stimulating Hormone (FSH) that helps to control the menstrual cycle and the production of eggs by the ovaries. In another embodiment, the hormones may include Luteinizing Hormone (LH) facilitating regulation of the menstrual cycle and ovulation. In men, the LH stimulates the production of testosterone, which plays a role in sperm production. In another embodiment, the hormones may include estrogen that plays a vital role in development and regulation of sex hormones, and its imbalance can cause several medical conditions. The level of estrogen changes during pregnancy. In another embodiment, the hormone may include Human Chorionic Gonadotropin (HCG) widely known as a pregnancy hormone, as it is produced in women during pregnancy. HCG levels may be assessed to determine the condition of pregnancy. In another embodiment, the hormone may include progesterone hormone which is responsible for the reception of the egg into the lining of the uterus. It is produced during ovulation in the ovaries. The drop in the level of progesterone if fertilization does not occur triggers the menstrual cycle once more. Progesterone level tests are conducted to help find causes of infertility, monitor effects of treatment with progesterone, determine ovulation state, access risk of miscarriages, monitor the correct functioning of the reproductive organs (such as ovaries and placenta) during pregnancy. Other conditions which are impacted by progesterone are adrenal gland issues, and certain cancers.

In one embodiment, the speech may have two types of attributes including, frequency and formants. The user's vocal tract is a tube or concatenation of tubes of varying cross-sectional area that is excited either at one end or at a point along the tube. The transfer function of energy from the excitation source to the output can be described in terms of the natural frequency or resonances of the tube. Such resonances are called formants for speech. The formants for speech may represent the frequencies that pass the most acoustic energy from the source of the output. Fant Gunnar et al., in a publication—"Acoustic Theory of Speech Production" 1990 (hereinafter "Reference 1") and Rabiner, L. and Schafer R. W. et al., in another publication—"Digital Processing of Speech Signals", Prentice-Hall, 1978 (hereinafter "Reference 2") defines formants as the spectral peaks of a sound spectrum |P(f)| of the voice. Further, the Reference 2, Prasanna, S. R. et. al, in another publication "Significance of Vowel Onset Point for Speech Analysis" and Bertil Malmberg et. al., in another publication "Manual of phonetics", North-Holland Publishing Company, (1968) collectively proposes that in speech science and phonetics, formant is also used to mean an acoustic resonance of the human vocal tract. Further, according to the Reference 2, the formant is often measured as an amplitude peak in the frequency spectrum of the sound, using a spectrogram. Furthermore, Meurer, Elisea et. al., in a publication "Menstrual Cycle Influences on Voice and Speech in Adolescent Females" (hereinafter "Reference 3") describes that the human vocal tract exhibits four or more major resonances, collectively known as "formants".

Further, Fant, Gunnar et. al in a publication "Acoustic Theory of Speech Production" Mouton & Co, The Hague, Netherlands, 1960 (hereinafter "Reference 4") describes that it has been described that users/speakers carry the anatomical makeup for speech movement and motor capability to achieve the complex movement as per the speech pattern. Furthermore, according to the Reference 4, a general rule in acoustic-articulatory relationship is that F1 frequency varies inversely with tongue height and F2 frequency or the difference between F2 and F1, varies inversely with tongue advancement. F2 variation is known to correspond to the front/back position of the tongue in articulatory terms. According to the Reference 3, it has been observed that a woman's menstruation cycle state changes can be studied using various phonetic parameters. Further, in the Reference 3, it has been discussed that the changes in formant frequencies were observed during the menstrual cycle in all four formants, however it was dominant in the fourth formant frequency, F4. Furthermore, according to the Reference 3, a significant change in F4 value was observed during the menstrual phase. It was also observed in the Reference 3 that vowel triangle are changes were corresponding to hormonal changes.

Dr. Will Styler et. al., in a publication "Using Praat for Linguistic Research" document version 1.7 defines VOT as a time between when the stop is released and when the voicing of the following vowel begins. Measuring this time, which can be positive (say, for the English voiceless aspirated stop ta), around zero (for the English "voiced" stop/d/, or, more commonly, the voiceless unaspirated [ta] around the world), or negative (for fully voiced stops, where voicing starts before the stop is released, as found in most non-English languages). Many languages classify their stops largely based on VOT, and it's often an excellent, more gradient empirical measure of the "voiced/voiceless" phonological distinction.

In one embodiment, VOP is the point in time at which the start of the vowel component of the utterance takes place in the speech signal.

In one embodiment, the analysing module 207 may perform an acoustic-phonetic analysis using the extracted speech features of the uttered speech segments in order to determine speech markers and the corresponding hormone level of the user. The analysing module 207 may use IPA phonemes in order to derive the speech markers that correspond to specific hormones and their levels. The IPA phonemes may include, but not limited to, semi-vowel, bilabial nasal consonant and voiced bilabial consonant.

In one embodiment, the analysing module 207 may determine the exact level of the FSH hormone in the user by selecting the Speech Markers associated with the hormone FSH and applying the mathematical relationship between those Speech Markers and the FSH hormone. The speech marker for FSH may depend on the index of the ratio of the pitch and formants of the semi-vowels, bilabial nasal consonant and voiced bilabial consonants.

In one embodiment, determination of the level of LH may be an index of speech marker that consists of the ratio of formants of the semi-vowels, bilabial nasal consonant and voiced bilabial consonants.

In one embodiment, determination of the level of estrogen may be an index of speech marker that consists of half of the difference of the formant values multiplied by frequency perturbation factor of the semi-vowels, bilabial nasal consonant and voiced bilabial consonants.

In one embodiment, determination of the progesterone level may be done from the speech markers of the semi-vowels, from the ratio of formants.

In one embodiment, determination of the ovulation period and peak may be done from the ratio of the consecutive higher formants.

Example 1:

In one exemplary embodiment, determination of the HCG speech markers may be done from the index of the sum of pitch and formant values of the semi-vowels, bilabial nasal consonant and voiced bilabial consonants. The nasal, vowel and semi vowel phonation are separated by filtering out noise and further speech features are extracted to calculate HCG levels as described in Table 1:

TABLE 1

| Consonant Phonation | Intensity (A) | Pitch (B) | Sum of Formant values (C) | TOTAL Sum (B + C − A) |
|---|---|---|---|---|
| Nasal | 43.9 | 202.97 | 7539.76 | 27945.37 |
| Voiced bilabial | 48.34 | 213.31 | 10707.03 | |
| Semi-vowel | 47.45 | 216.24 | 9109.07 | |

Example 2:

In another exemplary embodiment, determination of the Estrogen level speech markers may be done by determining index of a speech marker consisting of half of the difference of the formant values multiplied by frequency perturbation factor of the semi-vowels, bilabial nasal consonants and voiced bilabial consonants. The nasal, vowel and semi vowel phonation are separated, noise from phonation is filtered out and speech features are extracted to calculate Estrogen levels as mentioned below in the Table 2:

TABLE 2

| Consonant Phonation | Formant value at the start of menstruation cycle | Formant value at the start of follicular cycle | Difference (D) | Estrogen Level = [(Avg D)* frequency perturbation factor]/ 2 pgm/mLit |
|---|---|---|---|---|
| Nasal | 1137.4 | 1192.4 | 55 | 33.75 |
| Voiced bilabial | 2348.13 | 2399.13 | 51 | |
| Semi-vowel | 1813.11 | 1869.11 | 56 | |

Example 3:

In another exemplary embodiment determination of Follicle Stimulating Hormone (FSH) is derived as an index of a speech marker consisting of a ratio of the pitch and formants of the semi-vowels, bilabial nasal consonant and voiced bilabial consonants. Table 3 describes Follicle Stimulating Hormone (FSH) levels are calculated with the ratio of consecutive formants like mentioned below:

TABLE 3

| Consonant Phonation | ratio of (n + 1)/and $n^{th}$ consecutive formants | ratio of (n + 2) and (n + 1) consecutive formants | FSH Level IU/ L = ½[Avg (A + B)] |
|---|---|---|---|
| Nasal | 2.5 | 3.57 | 1.424166667 |
| Voiced bilabial | 2.2 | 2.74 | |
| Semi-vowel | 2.69 | 3.39 | |

Example 4:

In another exemplary embodiment, progesterone levels are derived with ratio of formants of nasal consonants multiplied by a mathematical coefficient (40 in this case), Table 4 describes progesterone levels are determination like mentioned below:

TABLE 4

| Nasal Consonant Phonation at days of menstruation cycle | ratio of (n + 1)/and n$^{th}$ consecutive formants as (A) | Progesterone Level ng/ml = (A * 40) |
|---|---|---|
| 17th day | 0.295 | 11.8 |
| 21st day | 0.503 | 20.12 |
| 25th day | 0.415 | 16.6 |

Example 5:

In one example, the start of ovulation and change in LH level is determined by analysing speech properties of isolated and noise free Nasal, bilabial, vowel phonation. Table 5 describes determination of LH level as mentioned below:

TABLE 5

| Phonation at days of menstruation cycle | ratio of (n + 1)/and nth consecutive formants A | ratio of (n + 2) and (n + 1) consecutive formants B | Diff A – B | Notes |
|---|---|---|---|---|
| 10th day | 1.15 | 6.14 | −4.99 | |
| 13th day | 4.46 | 1.75 | 2.71 | **** Change indicates LH surge and ovulation trigger |
| 17th day | 3.24 | 2.07 | 1.17 | |
| 21st day | 3.16 | 2.11 | 1.05 | |

In one embodiment, the report may be generated based on the level of different hormones. The report may be further transmitted to the user of the user device 104 via the network 102.

Figure 3:
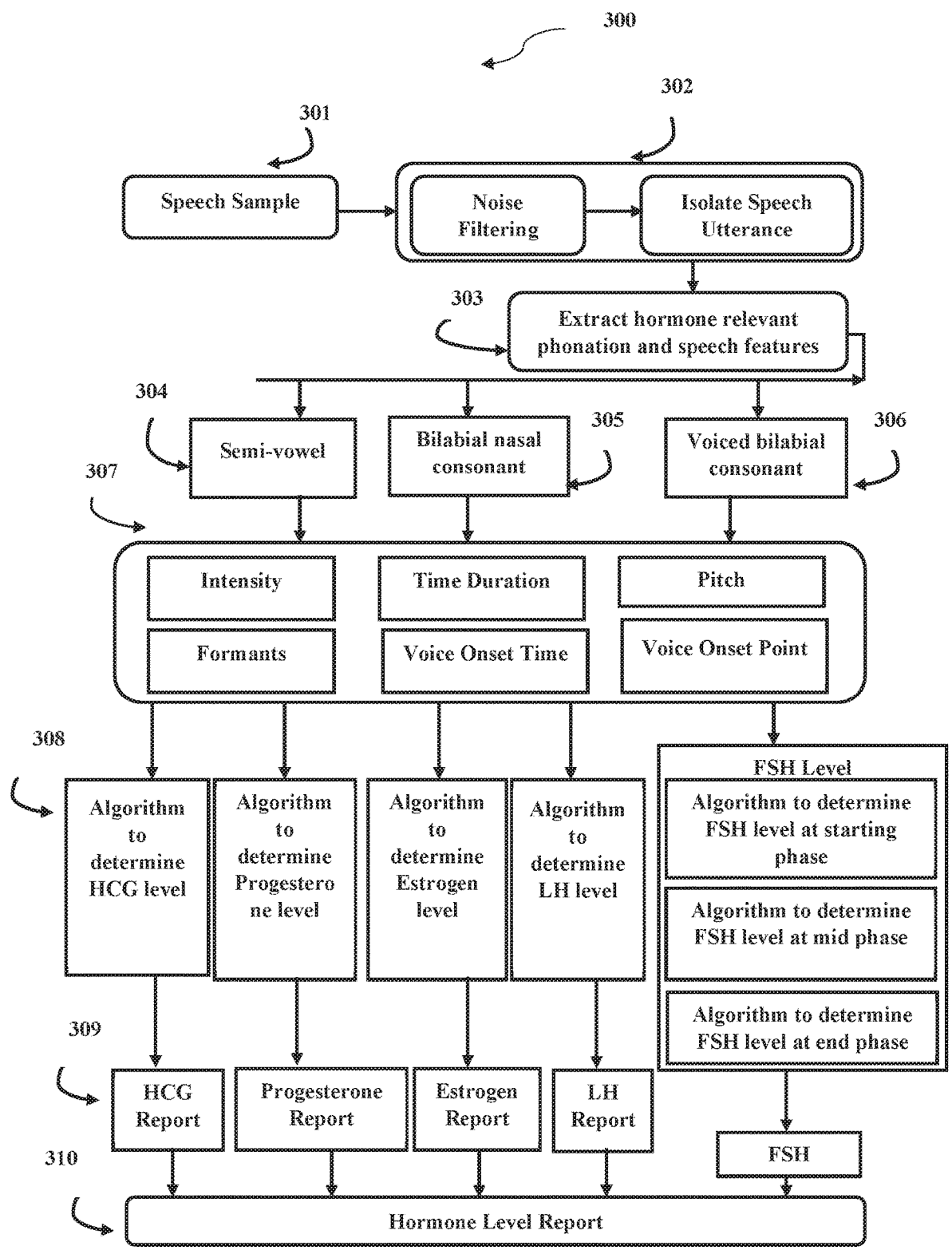
FIG. 3 illustrates a flow diagram depicting a method for estimating hormone levels and physiological conditions of a user by analysing speech samples of the said user, in accordance with an embodiment of a present disclosure.

FIG. 3 is a flow diagram depicting a method for estimating hormone level and physiological conditions of a user by analysing speech samples of the said user, in accordance with an embodiment of a present disclosure.

At block 302, the speech samples may be processed by the processing module 205. The processing module 205 may process the speech samples by isolating the one or more phonation segments from the speech samples. The processing module 205 may further filter the one or more phonation segments in order to remove noise from the one or more phonation segments. The processing module 205 may further isolate the uttered speech segments from the one or more phonation segments.

At block 303, the hormone relevant phonation and speech features may be extracted from the uttered speech segments by the extraction module 206.

At blocks 304, 305 and 306, the analysing module 207 may perform the acoustic-phonetic analysis using the extracted speech features of the uttered speech segments in order to determine speech markers and the corresponding hormone level of the user. In one embodiment, the analysing module 207 may use IPA phonemes in order to derive the speech markers that correspond to specific hormones and their levels.

At block 307, the analysing module 207 may further use the speech features for determining speech markers and the corresponding hormone level of the user.

At block 308, the analysing module 207 may execute different algorithms and/or mathematical formula to determine hormone levels of different hormones.

At block 309, separate reports may be generated based on the hormone level of each of the different hormones.

At block 310, the hormonal level report may be generated based on the level of different hormones. The report may be further transmitted to the user of the user device 104 via the network 102.

Although implementations for a system and method for estimating hormone level and physiological conditions of a user by analysing speech samples of said user have been described in language specific to structural features and/or methods, it is to be understood that the appended claims are not necessarily limited to the specific features or methods described. Rather, the specific features and methods are disclosed as examples of implementations for estimating hormone level and physiological conditions of a user by analysing speech samples of said user.

The invention claimed is:

1. A system (101) for detecting hormone level and physiological conditions of a user, the system comprising:
    a processor (201); and
    a memory (203) coupled with the processor, wherein the processor is configured to execute a plurality of programmed instructions stored in the memory (203), the plurality of programmed instructions comprising instructions for:
    interactively guiding a user to utter specifics of a speech via a user device (104) communicatively coupled with the processor (201);
    recording, via the user device, one or more speech samples associated with the user based upon the specifics of speech uttered by the user;
    isolating one or more phonation segments from the one or more speech samples to obtain one or more isolated phonation segments;
    filtering the one or more isolated phonation segments to remove noise from the one or more isolated phonation segments to obtain one or more filtered phonation segments;
    isolating one or more uttered speech segments from the one or more filtered phonation segments;
    performing acoustic-phonetic analysis of the one or more uttered speech segments to extract one or more speech features; and
    determining one or more speech markers and a corresponding hormone level of the user based upon the one or more speech features.

2. The system according to claim 1, wherein the specifics of speech comprises attributes selected from a group comprising of a frequency and formants, and wherein the specifics of speech comprises one or more of words, letters, and phonations.

3. The system according to claim 1, wherein the one or more speech features comprises utterance of the user, vowel and consonants under at least one of an isolated environment, a vowel consonant environment, or a consonant vowel environment, formants of the utterance, pitch of the utterance, vocal intensity of the utterance, speech quality of the utterance, vowel onset point (VOP), energy transition, values of dispersion and bandwidth, voice onset time (VOT), articulatory rate, shimmer, jitter, and spectrogram.

4. The system according to claim 1, wherein the one or more speech markers corresponding to the hormone level of the user are selected from a group comprising HCG speech marker, estrogen speech marker, progesterone speech marker, LH speech marker, and FSH speech marker, and wherein the one or more speech markers corresponding to the hormone level of the user are determined using International Phonetic alphabets (IPA) phonemes selected from a group comprising semi-vowel, bilabial nasal consonant, and voiced bilabial consonant.

5. The system according to claim 4, wherein a hormone level corresponding to the Follicle Stimulating Hormone (FSH) is an index of a speech marker consisting of a ratio of pitch and formants of the semi-vowel, the bilabial nasal consonant, and the voiced bilabial consonant.

6. The system according to claim 4, wherein a hormone level corresponding to the Luteinizing hormone (LH) is an index of a speech marker consisting of a ratio of formants of the semi-vowel, the bilabial nasal consonant, and the voiced bilabial consonant.

7. The system according to claim 4, wherein a hormone level corresponding to the estrogen hormone is an index of a speech marker consisting of half of a difference between two formants multiplied by frequency perturbation factor of the semi-vowel, the bilabial nasal consonant, and the voiced bilabial consonant.

8. The system according to claim 4, wherein a hormone level corresponding to the progesterone hormone is determined from a speech marker of the semi-vowel and from a ratio of formants of the bilabial nasal consonant.

9. The system according to claim 4, wherein a hormone level corresponding to the Human chorionic gonadotropin (hCG) hormone is an index of a speech marker consisting of sum of pitch and formants of the semi-vowel, the bilabial nasal-consonant, and the voiced bilabial consonant.

10. The system according to claim 1, wherein the programmed instructions further comprises programmed instructions for generating reports based upon the detection of the hormone level of the user, wherein the reports generated comprises separate reports for one or more of estrogen, progesterone, Luteinizing Hormone (LH), Follicle Stimulating Hormone (FSH), and other human body hormones.

11. A method for detecting hormone level and physiological conditions of a user, the method comprising:
   interactively guiding, via a user device communicatively coupled with a processor, a user to utter specifics of a speech;
   recording, via the user device, one or more speech samples associated with the user based upon the specifics of speech uttered by the user;
   isolating, via the processor, one or more phonation segments from the one or more speech samples to obtain one or more isolated phonation segments;
   filtering, via the processor, the one or more isolated phonation segments to remove noise from the one or more isolated phonation segments to obtain one or more filtered phonation segments;
   isolating, via the processor, one or more uttered speech segments from the one or more filtered phonation segments;
   performing, via the processor, acoustic-phonetic analysis of the one or more uttered speech segments to extract one or more speech features; and
   determining, via the processor, one or more speech markers and a corresponding hormone level of the user based upon the one or more speech features.

12. The method according to claim 11, further comprising generating, via the processor, reports based upon the detection the hormone level of the user, wherein the reports generated comprises separate reports for one or more of estrogen, progesterone, Luteinizing Hormone (LH), Follicle Stimulating Hormone (FSH), and other human body hormones.

* * * * *